United States Patent [19]

Blouin

[11] Patent Number: 4,587,358

[45] Date of Patent: May 6, 1986

[54] PRODUCTION OF HIGH-STRENGTH, STORAGE-STABLE PARTICULATE UREA

[75] Inventor: Glenn M. Blouin, Florence, Ala.

[73] Assignee: Tennessee Valley Authority, Muscle Shoals, Ala.

[21] Appl. No.: 769,095

[22] Filed: Aug. 26, 1985

[51] Int. Cl.$^4$ ..................... C07C 85/26; C07C 126/10
[52] U.S. Cl. ......................................... 564/3; 564/63; 564/32
[58] Field of Search ................................ 564/3, 63, 32

[56] References Cited

PUBLICATIONS

Chem. Abs: 85:165669t, Bleskina et al, Zakreplenie Uplotnenie Grunt. Stroit., Mater., Vses., Soveshch., 8th (1974) pp. 165–168.

Primary Examiner—Charles F. Warren
Assistant Examiner—R. A. Picard
Attorney, Agent, or Firm—Robert A. Petrusek

[57] ABSTRACT

One approach to improving storage stability, particularly that attribute characterized by reduction in the tendency for caking during storage of freshly prepared urea particles such as granules, is to treat the surface areas of the freshly prepared particles/granules with appropriate amounts and kinds of conditioning agents. This approach does not address the problem of increasing the hardness of the particles to impart improved high-strength characteristics thereto. A second approach to this problem of improving storage stability of urea granules is to admix and/or react certain anticaking and hardness improving additives into or with the urea melt prior to the solidification of urea particulates therefrom. The instant invention is directed to this second approach of imparting to the ultimately prepared urea particles both improved anticaking and hardness (as opposed to being easily crushed, i.e., friable) characteristics by means of addition to the urea melt of certain additives. The additives discovered and now disclosed as a principal feature of the instant invention are from the class of compounds known as lignosulfonates and are added in such minute quantites that although they impart the improved desired characteristics to the particles formed from said melt, they neither add nor detract substantially from other properties thereof.

7 Claims, No Drawings

PRODUCTION OF HIGH-STRENGTH, STORAGE-STABLE PARTICULATE UREA

The invention herein described may be manufactured and used by or for the Government for governmental purposes without the payment to me of any royalty thereof.

INTRODUCTION

The chemical fertilizer industry has long recognized the desirability of fertilizer products containing relatively high nitrogen levels in a granular form that may be closely sized and which closely sized granules exhibit characteristics of hardness and friability sufficient to prevent the fracturing thereof during storage and/or subsequent handling. The importance of maintaining a predetermined, closely sized range of granules will be appreciated when it is realized that there is always the possibility of segregation of granules if such are later incorporated in the production of bulk-blend fertilizer materials. The importance of uniform particle size in the preparation of bulk blends is discussed more thoroughly in TVA reprint Z-49 reprinted from the proceedings of TVA Fertilizer Bulk Blending Conference, Aug. 1-2, 1973, "Quality Control in a Bulk Blending Plant." Among the solid forms of N sources, urea is currently the leading one accounting for about 35 percent of total solid fertilizer N used in the United States, ahead of ammonium nitrate, which accounts for about 32 percent of total solid fertilizer N used, as reported by the USDA for 1980 (Consumption of Commercial Fertilizers, 1955-1980 fiscal years; Annual Reports; Economics, Statistics, and Cooperative Service; Crop Reporting Board, U.S. Department of Agriculture, Washington, D.C.). The corresponding values for 1960 are 9.5 percent and 61 percent, respectively, which indicates the faster relative growth of urea versus ammonium nitrate. There are several characteristics of urea that are considered desirable and that have caused a switch in the fertilizer industry in favor of urea over ammonium nitrate. Urea has a higher plant nutrient analysis than ammonium nitrate (46 percent vs 33.5 percent N, respectively). Urea is classified as a nonhazardous material whereas ammonium nitrate, an explosive compound, is barred from barge transportation which is relatively less expensive than other forms of surface transportation and therefore a most desirable mode for providing for the movement of bulk materials, including solid fertilizers. There is a considerable amount of flexibility in the end uses of urea other than fertilizer use in the off-season, particularly as animal feedstock and in certain other chemical processing. In contrast, ammonium nitrate production facilities operate at levels well below capacity in the off-season. A further point in favor of urea production is the added cost associated with air pollution abatement which is required for ammonium nitrate production, it being substantially higher than that required for urea production. All of these factors supra, favoring production of urea rather than ammonium nitrate, are predominantly nonagronomic. From an agronomic point of view, urea has certain characteristics that make it less desirable than ammonium nitrate. Among those is that when urea is surface applied on soil, it quickly hydrolyzes to ammonium carbonate, and a substantial amount of the ammoniacal nitrogen can be lost by volatilization. Losses as high as 79 percent have been reported by G. L. Terman in 1979, "Volatilization Losses of Nitrogen as Ammonia from Surface-Applied Fertilizers, Organic Amendments, and Crop Residues," Advances in Agronomy, Vol. 31, 189-223, Academic Press. The magnitude of such losses is especially high when urea is used on alkaline soils, on sandy soils (versus loamy or clayey soils), and on soils undergoing desiccation when hot, dry weather prevails after urea is applied. From a chemical engineering processing point of view, urea also has certain characteristics that make it less than totally desirable. Urea may be produced from any of a variety of known commercial applications of the basic reaction of ammonia with carbon dioxide at elevated temperatures and pressures. For some of such commercial applications, see Kirk-Othmer, Encyclopedia of Chemical Technology, 3rd Edition, Volume 23 (1983) pp. 551-562. As may be seen, the reaction products from such commercial processes normally are 70 to 80 percent aqueous urea solutions which solutions can subsequently be processed to form solid urea particulates, such as granules, in any number of ways. Also see Kirk-Othmer, 3rd Edition, Volume 23 (1983) pp. 562, 564-572. The resulting urea particles/granules produced therefrom exhibit at least two annoying tendencies from an engineering processing standpoint, to wit, caking and friability. The tendency to cake will, of course, vary depending on the manner in which the urea solution has been processed into urea granules. However, such tendency oftentimes makes it infeasible for the resulting urea product to be stored and transported in bulk without added processing considerations being required else the initially prepared, free-flowing product may change to a dense, solid, essentially singular mass in the storage pile. The second annoying tendency of urea granular products produced by the basic reaction supra is their exhibited tendency to break easily into smaller particles and substantial amounts of dust while being handled, transported, and applied to the intended soil environment. For instance, even if the granules hold together during storage and transportation and thereby lend themselves to satisfactory particle size distribution for the preparation of nonsegregable bulk blend supra, their introduction into modern, rotating turbine fan type field distribution equipment introduces the added, unwanted consideration of breakage therein and subsequent uneven distribution therefrom. For instance, urea particles which have not been properly treated for exhibiting improved hardness characteristics are oftentimes shattered to an appreciable degree when they are introduced into most common types of equipment with the result that the small pieces resulting therefrom fall in a shorter trajectory from the distributor and thusly form a more narrow and a more concentrated swath on the soil surface than is originally intended.

In efforts to overcome these major disadvantages relating to caking and breakage tendencies of particulate/granular urea materials intended for fertilizer applications, the art has turned to two basic approaches. In the first approach, the freshly prepared urea particles are surface treated with any number of a variety of materials, such as clays or diatomaceous earth. This first approach addresses only the problem of improving the anticaking characteristics of the urea material by the addition onto the surface thereof of additives, which additives may, in turn, incorporate foreign elements into or onto the urea which in themselves are, in some instances, not adequately compatible for the purpose for which the urea may ultimately be used. In the second approach to this problem, producers of urea have turned to the incorporation into either the concentrated urea liquor solution or melt produced therefrom of additives which impart to the subsequently formed urea particulates either improved anticaking characteristics or improved nonfriable characteristics, i.e., hardness or resistance to breaking, or most desirably both.

In more recent times, the fertilizer industry has seen increasing demands concerning the mechanical strength of the produced and delivered particulate urea. There are several reasons for this consideration relating to hardness or mechanical strength having greater emphasis, including the fact that urea is now exposed to substantially greater mechanical strains due to the modern methods of handling and transportation now utilized which, in turn, result in more crushing of the urea granules and the undesirable production of greater amounts of dust. Apart from increasing requirements for a nondusting product during the handling thereof, including field distribution, from a purely health and safety consideration, modern day economics dictate that the product material must not be crushable and therefore dust-forming, either during the stage of the handling of same, during the bulk blending thereof, or during the ultimate application thereof to the soil environment.

BACKGROUND OF THE INVENTION

1. Field of the Invention

The present invention relates to the production of an improved particulate urea product, normally in granular form, having both eminently improved anticaking and hardness characteristics. The modus operandi of the instant invention follows the second embodiment discussed supra in the introduction thereof, to wit, directly or indirectly incorporating into the urea melt certain new, novel, and heretofore unknown additive materials (unknown in the sense that these materials, although commonly available, have heretofore been unrecognized as having desirable characteristics of imparting to the formed urea particles the improved characteristics realized by practice of the instant invention).

2. Description of the Prior Art

As noted above, numerous investigators have discovered, taught, and disclosed a plethora of conditioning agents which may be added either directly to the anhydrous molten urea melt or indirectly thereto by means of incorporating same into the synthesis liquor before said melt is processed to the particulates formed therefrom to either improve the anticaking characteristics; the nonfriable characteristics; and/or, allegedly in some instances, improvements in both of these areas. These problems, as well as other attendant considerations for storage, handling, and application characteristics of granular/particulate urea, have been alleviated, to a significant degree, by the addition to the urea melt of low concentrations, e.g., 0.1 percent to 0.5 percent, by weight, of formaldehyde, which formaldehyde reacts with the urea to form urea-formaldehyde addition products. It has long been known that these addition products or compounds act to modify the crystallization pattern of the substantilly anhydrous molten urea during the subsequent formation thereof into solid particles by prilling, granulation, or other means to effect the production of substantially harder, abrasion-resistant particulates. Of particular interest from the practical aspects of this approach for methods employing the addition of formaldehyde, are those taught in the following references: Allgeuer and Weintrotter, U.S. Pat. No. 3,112,343, Nov. 26, 1963; Van Hijfte et al, U.S. Pat. No. 4,160,782, July 10, 1979; and Elstrom et al, U.S. Pat No. 4,204,053, May 20, 1980. Perusal of the above references reveals teachings of the formation of various concentrated solutions of a urea-formaldehyde reaction product(s) which are subsequently added in predetermined and desired amounts to the urea synthesis liquor, either before or after concentration thereof, or to the essentially anhydrous molten melt prior to ultimate formation of the desired particulate urea.

Although many of the problems associated with friability and caking of such formed particulate urea may be alleviated, as indicated above, to a significant degree by the addition of such relatively low concentrations of principally formaldehyde to either the urea synthesis liquor or the essentially anhydrous molten melt, modern day health and safety considerations under the genesis of modern environmental concerns have led or are presently leading to the close scrutiny of the many chemicals, organic as well as inorganic, utilized in the fertilizer-food chain. It is my understanding that formaldehyde is now designated as a toxic and/or carcinogenic material by the U.S. Environmental Protection Agency (EPA) which designation may well lead to either the restriction or total prohibition of the use of formaldehyde in agriculture products, including its use as a conditioning agent in the preparation of urea for fertilizer or animal feed preparation purposes.

SUMMARY OF THE INVENTION

The instant invention relates to a vastly improved urea particulate product preferable in the form of granular urea eminently useful for either direct application to the soil or as an intermediate product for the subsequent incorporation with other fertilizer materials into bulk blends. The product of the instant invention has imparted thereto vastly improved anticaking and nonfriable characteristics which render it at least on par with fertilizer granules produced by the prior incorporation into either the synthesis liquor or the essentially anhydrous molten melt of the material, formaldehyde either alone or in combination with certain organic modifiers.

The gist underlying the concept of the instant invention is the discovery that certain compounds of the generic system of lignin chemicals known as lignosulfonates, may be completely substituted for materials such as formaldehyde supra. Not only does the substitution of these lignosulfonates for such materials as formaldehyde reduce the cost of the product, but they completely eliminate any health and safety considerations in that they are presently approved for use as additives in animal feed products. As will be seen infra, although the amounts of lignosulfonate that must be incorporated into the urea synthesis liquor and/or melt ranges preferably from about 0.1 percent to about 1.0 percent by weight of the product urea and thereby on the high range require twice as much additive material per ton of product as does the practice employing the use of formaldehyde, the sources of lignosulfonates as by-products from the paper pulping industry provide an abundant, relatively inexpensive additive whereby the cost of the ultimate product is reduced in that the total cost of additive may be reduced to about one-third, depending upon the form and amount used. In addition, the hardness of the resulting urea granules is sometimes greater then the materials made with formaldehyde, thereby resulting in a product having higher abrasion resistance and greatly improved nonfriable properties.

OBJECTS OF THE INVENTION

It is therefore the principal object of the present invention to develop a new method and/or means for producing particulate urea such as granules thereof wherein the anticaking and nonfriable characteristics thereof are at least as great as that realized when urea prills and granules are produced by the incorporation into the urea synthesis liquor or anhydrous molten melt of materials such as formaldehyde.

Another principal object of the instant invention is to develop a new method and/or means for producing particulate urea such as granules thereof wherein the anticaking and nonfriable characteristics (hardness) thereof are at least as great as that realized when urea prills and granules are produced by the incorporation into the urea synthesis liquor or anhydrous molten melt of materials such as formaldehyde, and wherein the utilization of such formaldehyde is substantially eliminated therefrom and additive materials are substituted therefor which may be several times more cost effective than said formaldehyde.

A still further object of the present invention is to develop a new method and/or means for producing particulate urea such as granules thereof wherein the anticaking and nonfriable characteristics thereof are at least as great as that realized when urea prills and granules are produced by the incorporation in the urea synthesis liquor or anhydrous molten melt of materials such as formaldehyde, wherein the utilization of such formaldehyde is substantially eliminated therefrom and additive materials are substituted therefor which may be several times more cost effective than said formaldehyde and wherein said new additive material alleviates any undesirable concerns from the standpoint of environmental aspects, including those aspects relating to toxicity and carcinogenicity.

Still further and more general objects and advantages of the present invention will appear from the more detailed description set forth below, it being understood, however, that this more detailed description is given by way of illustration and explanation only, and not necessarily by way of limitation since various changes therein may be made by those skilled in the art without departing from the true spirit and scope of the present invention.

DESCRIPTION OF THE PREFERRED EMBODIMENTS

Modern day environmental concerns have led to the close scrutiny of many chemicals used in the fertilizer-food chain, and formaldehyde is now designated as a toxic and carcinogenic chemical by the EPA. This may well lead to the restricted use or total prohibition of formaldehyde in agriculture (fertilizers) by EPA.

The shortcomings and defects of the prior art as it relates to the "second" approach taken by the instant invention are now obviated by the practice thereof by the expedient, briefly stated, of incorporating into the urea synthesis liquor, either from the synthesis section or the concentration (evaporation) section, or into the particulate-forming section, i.e., the molten urea melt, during the manufacturing process, compounds from the generic system of lignin chemicals known as lignosulfonates; which are commonly produced as metal or ammonium salts of lignosulfonic acid, a by-product of the sulfite pulp paper process. These materials are for the most part water-soluble and soluble in the urea solutions mentioned above and are added in such small quantities that, while the desired physical properties—hardness, and storage stability (nonagglomeration in long-term storage)—are imparted thereto, the nitrogen content and other useful purposes to which the so treated urea may be put, are not significantly reduced and the cost oftentimes is also significantly reduced. The salts of lignosulfonic acid are noncarcinogenic and nontoxic it being understood that one of their many uses is as additives for inclusion into animal feed products and food-packaging materials.

In carrying out the practice of the present invention as outlined above, use is made of the water- and urea-soluble metal or ammonium lignosulfonates, particularly calcium lignosulfonate, which is generally the lowest cost material in this large group of chemicals in amounts of, at most, 5 percent of the weight of the urea, and preferably from only about 0.1 percent to about 1.0 percent by weight of the product urea.

The lignosulfonates are, as previously indicated, paper manufacturing by-products that are: in solution form; inexpensive relative to formaldehyde; soluble in molten urea at the necessary levels of addition; and used directly as formulated in the solution form by the paper manufacturer. No intermediate processing of said lignosulfonates is required, although spray-drying thereof to produce a powdered form of the lignosulfonate may be performed without diminishing its effect herein. The same would apply to the solution forms of the lignosulfonates in which off-grade urea particles were dissolved simply to reduce the water content thereof. In preparing the final product according to the teachings of the instant invention, an anhydrous urea melt, or urea containing a low percentage of water, is easily intimately mixed with the soluble lignosulfonate in the necessary ratio and the mixture is transformed into particulate urea by any of the many means well known and practiced in the art, e.g., prilling or melt granulation. Since the lignosulfonate is soluble in the urea melt within the limits indicated supra, there results a completely homogeneous distribution of the lignosulfonate in each particle of urea subsequently formed after the mixing step.

EXAMPLES

In order that those skilled in the art may better understand how the present invention can be practiced, the following examples are given by way of illustration only and not necessarily by way of limitation, since numerous variations thereof will occur and will undoubtedly be made by those skilled in the art without substantially departing from the true and intended scope of the instant invention herein taught and disclosed.

Although the data taught, disclosed, and discussed in the following three examples reflects on specific use of the material calcium lignosulfonate, the instant invention is, of course, not necessarily limited thereto in that a number of other water-soluble metal lignosulfonates, as well as certain ammonium lignosulfonates, are considered herein. It is suggested that the emphasis herein on the use of such calcium lignosulfonate is quite appropriate in that it is perhaps the form most commonly available from the paper pulping industry and normally most economically attractive. Examples of other lignosulfonates that are technically at least substantially as effective are sodium lignosulfonates of both low and high lignosulfonic acid contents, each with low or high transition metal contents; sodium lignosulfonates containing sodium salts of hexose and pentose reversion acids; calcium lignosulfonates with both low and high wood sugar contents; sodium-calcium lignosulfonates; calcium lignosulfonates containing high carbohydrate contents; modified calcium lignosulfonates containing iron, zinc, magnesium or manganese; and ammonium lignosulfonate. Many of these metal or ammonium salts of lignosulfonic acid are commercially available in either the aqueous solution or dry powder forms.

EXAMPLE I 200-gram batches of molten urea at 140° C. were treated by adding small amounts of calcium lignosulfonate, as indicated in the tabulation below, with thorough mixing for about 2 minutes. The admixture was then poured into porcelain color plates where it quickly solidified therein into hemispherical-like segments about 8 mm thick and 20 mm wide. After cooling and aging 4 hours, the hemispherical segment pellets were tested for hardness by compressing them in a compression tester to the breaking point. Untreated urea and urea containing 0.5 percent by weight of formaldehyde were similarly produced and tested as control samples. The results are given in Table I below.

TABLE 1

| Additive | None (Untreated) | Formaldehyde | Calcium lignosulfonate as Powder | Calcium lignosulfonate as 58% Solution |
|---|---|---|---|---|
| Weight % additive in urea | 0 | 0.50 | 0.75 | 0.75 |
| Crushing strength, kg | 8.3 | 21.80 | 11.10 | 21.90 |
| Increased strength over untreated urea, % | — | 163 | 33 | 165 |
| Cost of additive per metric ton of urea, $ | — | 2.66 | 2.25 | 0.90 |

From the above data it is apparent that the solution form of calcium lignosulfonate yielded a crushing strength (hardness) that was much greater than that of untreated urea and was equal to that of the formaldehyde-treated urea. The cost of the calcium lignosulfonate (solution form) per ton of treated urea is much lower than that for formaldehyde. The powdered form of calcium lignosulfonate yielded a hardness about 33 percent greater than that of untreated urea and at a cost somewhat lower than that for formaldehyde.

EXAMPLE II

The above tests (Example I) were intended as screening tests to determine the relative applicability of a number of urea conditioning additives for subsequent testing on a larger scale, i.e., at 1360 kilograms to 1800 kilograms per hour in the TVA falling curtain drum melt granulation process. Again, the purpose of the pilot-plant tests was to compare the lignosulfonate with formaldehyde as a conditioning agent for particulate urea. The results of the pilot-plant tests with powdered calcium lignosulfonate are given in Table II below (a control test using formaldehyde is given for comparison).

TABLE II

Pilot-Plants Tests to Compare Calcium Lignosulfonate with Formaldehyde as a Conditioning Addition Production of Granular Urea

| Additive | Formaldehyde (Run 151) | Calcium lignosulfonate powder (Run 163) |
|---|---|---|
| Test duration, h | 3.5 | 3.5 |
| Urea melt[a] | | |
| Feed rate, lb/h | 4,020 | 3,000 |
| Additive feed rate, % of melt rate | 0.4 | 0.85 |
| Cost of additive, $/ton urea | 2.13 | 2.55 |
| Granulator | | |
| Recycle feed, lb/h | 3,600 | 2,700 |
| Recycle ratio, lb/lb product | 0.9 | 0.9 |
| Temp, °F. | | |
| Urea melt | 300 | 297 |
| Recycle | 143 | 125 |
| Product | 229 | 222 |
| Cooler discharge temp, °F. | 150 | 140 |
| Product | | |
| Discharge rate (nominal), lb/h | 4,000  4,000 | 3,000 |
| Chemical analyses, wt % | | |
| Total N | 46.1 | 45.8 |
| Biuret | 1.0 | 1.0 |
| H2O (Karl Fischer) | 0.08 | 0.10 |
| Physical properties | | |
| Crushing strength, lb[b] | 7.2 | 8.0 |
| Moisture penetration, cm | 21.0 | 13.5 |
| Moisture absorption, mg/cm$^2$ | 534 | 418 |
| Critical relative humidity, % | 65–70 | 65–70 |

[a]Urea prills melted continuously and additive metered to agitated melt vessel.
[b]Measured after 6 or more days.

Operation of the plant with the powdered lignosulfonate was entirely similar to that with formaldehyde in that dust formation in the granulator was suppressed adequately. The granules produced by the practice of the instant invention were somewhat harder than the product containing formaldehyde.

In storage the products all remained free-flowing even under load for an extended period of time. A granular urea product made earlier that contained neither additive conditioner was badly caked under similar storage conditions.

As is evident from the above, the essence of the present invention is in the substitution of an equally effective, nontoxic lignosulfonate, such as powdered calcium lignosulfonate, for potentially toxic formaldehyde, the current commercial particulate urea conditioning agent, into the urea being processed and doing so at a cost per ton of urea only moderately higher than that for formaldehyde. In practice, 0.6 percent lignosulfonate at $1.80 per ton urea should be satisfactory.

EXAMPLE III

Continuing the comparison of the lignosulfonates with formaldehyde, as suggested by the results of laboratory tests (Example I) supra, pilot-plant tests as discribed in Example II also supra were conducted using aqueous calcium lignosulfonate solution (versus powder, Example II) at two levels of addition (concentration). The results of the pilot-plant tests are given in Table III below. The control test using formaldehyde, given in Table II supra, is repeated for convenience.

TABLE III

Pilot-Plants Tests to Compare Calcium Lignosulfonate with Formaldehyde as a Conditioning Additive in Production of Granular Urea

| Additive | Formaldehyde (Run 151) | Calcium lignosulfonate (solution 58% solids) (Run 164A) | Calcium lignosulfonate (solution 58% solids) (Run 164B) |
|---|---|---|---|
| Test duration, h | 3.5 | 1.5 | 2.7 |
| Urea melt[a] | | | |
| Feed rate, lb/h | 4,020 | 3,000 | 3,000 |
| Additive feed rate, % of melt rate | 0.4 | 0.61 | 0.81 |
| Cost of additive, $/ton urea | 2.13 | 0.73 | 0.97 |
| Granulator | | | |
| Recycle feed, lb/h | 3,600 | 2,700 | 3,000 |
| Recycle ratio, lb/lb product | 0.9 | 0.9 | 1.0 |
| Temp, °F. | | | |
| Urea melt | 300 | 295 | 295 |
| Recycle | 143 | 125 | 125 |
| Product | 229 | 205 | 220 |
| Cooler discharge temp, °F. | 150 | 130 | 141 |
| Product | | | |
| Discharge rate (nominal), lb/h | 4,000 | — | — |
| analyses, wt % | | | |
| Total N | 46.1 | 45.8 | 45.9 |
| Biuret | 1.0 | 0.8 | 1.0 |
| H2O (Karl Fischer) | 0.08 | 0.14 | 0.18 |
| Physical properties | | | |
| Crushing strength, lb[b] | 7.2 | 5.6 | 6.2 |
| Moisture penetration, cm | 21.0 | 13.5 | 14.0 |
| Moisture absorption, mg/cm$^2$ | 534 | 412 | 407 |
| Critical relative humidity % | 65–70 | 65–70 | 65–70 |

[a] Urea prills melted continuously and additive metered to agitated melt vessel.
[b] Measured after aging 6 or more days.

Operation of the pilot plant with the calcium lignosulfonate solution was entirely similar to that with formaldehyde in that dust formation in the granulator was suppressed adequately. Although the granules produced by the practice of the instant invention were not quite as hard as was the product containing formaldehyde, the hardness achieved (5.6 to 6.2 pounds) was considered to be entirely satisfactory (see TVA Bulletin Y-147, October 1979).

In storage, the products behaved in a fashion entirely similar to that described in Example II supra.

As is evident from the above, the essence of the present invention is in the substitution of an effective, non-toxic lignosulfonate, such as an aqueous solution of calcium lignosulfonate, for potentially toxic formaldehyde, the current commercial particulate urea conditioning agent, into the urea being processed, and doing so at a lower cost per ton of urea.

The particular water soluble lignosulfonate described in detail herein, i.e., calcium lignosulfonate, of course, does not constitute the entire scope of the instant invention per se nor does the method of production of such materials since both may take a variety of forms.

The hardness and free-flowing, storage-stable particulate urea containing at most 5 percent, and most preferably from about 0.1 percent to about 0.8 percent, by weight of the so-treated urea, of lignosulfonates that are highly soluble in molten urea or concentrated aqueous solutions of urea, according to the present invention is clearly established as being advantageous to present practice in the art.

INVENTION PARAMETERS

After sifting and winnowing through the data supra, as well as other results and operations of my new, novel, and improved method for effecting the production of particulate urea, including granules displaying eminently improved anticaking and nonfriable characteristics realized through the substitution for the commonly used urea melt additive, formaldehyde, commonly available materials heretofor unrealized as to their potential herein discovered, the operating variables and preferred conditions for carrying out my process are summarized below:

| Variables | Operating Limits | Preferred Limits | Most Preferred Limits |
|---|---|---|---|
| Wt. %, urea - Urea synthesis liquor (standard plant conditions) | 65–85 | 70–80 | 75 |
| Temp. (°F.) - Urea synthesis liquor (standard plant conditions) | 150–250 | 195–210 | 200 |
| Wt. %, urea - Urea concentrator discharge (standard plant conditions) | 95–100 | 99–100 | 99.7 |
| Temp. (°F.) - Urea concentrator discharge (standard plant conditions) | 260–330 | 280–310 | 285–295 |
| Wt. %, Lignosulfonate solids concentration in urea particles | 0.1–5.0 | 0.1–1.0 | 0.4–0.8 |
| Retention time in urea melt prior to solidification process (min) | 1–30 | 1–15 | 1–5 |
| Feed lignosulfonate, % H2O in powder | 0–20 | 0–5 | 0–1 |
| Feed lignosulfonate, % solids in solution | 40–70 | 50–70 | 60–70 |

While I have shown and described particular embodiments of my invention, modifications and variations thereof will occur to those skilled in the art. I wish it to be understood therefore that the appended claims are intended to cover such modifications and variations which are within the true scope and spirit of my invention.

What I claim as new and desire to secure by Letters Patent of the United States is:

1. An improved product resulting from the production of hard, free-flowing, storage-stable particulate urea, each particle thereof being substantially homogeneous and consisting essentially of an admixture of urea and a water-soluble metal or ammonium salt of lignosulfonic acid, the quantity of said salt ranging from about 0.1 percent to about 5 percent by weight of said admixture.

2. The improved hard, free-flowing, storage-stable particulate urea product of claim 1 wherein said salt ranges from about 0.4 percent to about 0.1 percent by weight of said admixture.

3. The improved hard, free-flowing, storage-stable particulate urea product of claim 2 wherein said salt ranges from about 0.4 percent to about 0.8 percent by weight of said admixture.

4. An improved method of imparting to particulate urea the properties of substantially increased resistance to breaking under impact, of non-agglomeration during prolonged storage, and of reduced dusting during melt-granulation process to form said particulates, which improved method comprises the steps of:

(1) mixing water-soluble metal or ammonium lignosulfonates or both into an essentially anhydrous molten melt of urea or highly concentrated urea synthesis solutions subsequently utilized to produce said melt until a homogeneous mixture thereof results and (2) subsequently converting said melt into particulate form, said improved method characterized by the fact that the resulting individual particulates contain from about 0.1 percent to 5.0 percent by weight of said lignosulfonate.

5. The improved method of claim 4 wherein the amount of lignosulfonate admixed with said anhydrous molten urea melt or into said synthesis solution utilized for the production thereof is utilized in amounts to range from 0.1 percent to about 1.0 percent by weight of said lignosulfonate in the urea product.

6. The improved method of claim 5 wherein the amount of lignosulfonate admixed with said anhydrous molten urea melt or into said synthesis solution utilized for the production thereof is utilized in amounts to range from 0.4 percent to about 0.8 percent by weight of said lignosulfonate in the urea product.

7. The process of claim 4 wherein said metal lignosulfonate is calcium lignosulfonate.

* * * * *

UNITED STATES PATENT AND TRADEMARK OFFICE
CERTIFICATE OF CORRECTION

PATENT NO. : 4,587,358
DATED : May 6, 1986
INVENTOR(S) : Glenn M. Blouin

It is certified that error appears in the above-identified patent and that said Letters Patent are hereby corrected as shown below:

Column 8, TABLE II, line 23, under the column heading "Formaldehyde (Run 151)" and in line with Discharge Rate "4,000 4,000" should be -- 4,000 --

Column 8, table II, footnote b, after "Measured after" and before "6 or more days" insert -- aging --

Column 8, line 63, "dis-" should be -- des- --

Column 9, line 25, table III, under the column heading "Additive" and before "analyses, wt %" insert -- Chemical --

Column 10, line 57, "0.4 percent" should be -- 0.1 percent --
Column 10, line 57, "0.1 percent" should be -- 1.0 percent --

Signed and Sealed this

Ninth Day of December, 1986

*Attest:*

DONALD J. QUIGG

*Attesting Officer*  *Commissioner of Patents and Trademarks*